United States Patent
Emoto

(10) Patent No.: US 10,689,310 B2
(45) Date of Patent: Jun. 23, 2020

(54) METHOD FOR PRODUCING ALPHA-OLEFIN LOW POLYMER

(71) Applicant: Mitsubishi Chemical Corporation, Chiyoda-ku (JP)

(72) Inventor: Hiroki Emoto

( * ) Notice: Subject to any disclaimer, the term of this patent is extended or adjusted under 35 U.S.C. 154(b) by 0 days.

(21) Appl. No.: 15/715,505

(22) Filed: Sep. 26, 2017

(65) Prior Publication Data
US 2018/0016205 A1 Jan. 18, 2018

Related U.S. Application Data

(63) Continuation of application No. PCT/JP2016/059246, filed on Mar. 23, 2016.

(30) Foreign Application Priority Data

Mar. 27, 2015 (JP) .................. 2015-006777

(51) Int. Cl.
*C07C 2/26* (2006.01)
*B01J 31/22* (2006.01)
(Continued)

(52) U.S. Cl.
CPC ............ *C07C 2/26* (2013.01); *B01J 31/0231* (2013.01); *B01J 31/0244* (2013.01); *B01J 31/22* (2013.01);
(Continued)

(58) Field of Classification Search
CPC .............. B01J 31/0244; B01J 31/0231; B01J 2231/20; C07C 11/107; C07C 2531/02
See application file for complete search history.

(56) References Cited

U.S. PATENT DOCUMENTS 5,750,817 A 5/1998 Tanaka et al.
5,856,612 A * 1/1999 Araki ................... B01J 31/0237
585/512
(Continued)

FOREIGN PATENT DOCUMENTS

CN 1182729 A 5/1998
CN 101547941 A 9/2009
(Continued)

OTHER PUBLICATIONS

International Search Report dated Jun. 28, 2016 in PCT/JP2016/059246, filed on Mar. 23, 2016 (with English Translation).
(Continued)

*Primary Examiner* — Ali Z Fadhel
(74) *Attorney, Agent, or Firm* — Oblon, McClelland, Maier & Neustadt, L.L.P.

(57) ABSTRACT

An object of the present invention is to provide a method for efficiently producing an α-olefin low polymer at a high α-olefin low polymer selectivity and a high α-olefin low polymer yield with suppressing the deterioration of catalytic activity with time, and the invention relates to a method for producing an α-olefin low polymer, which comprises performing a low polymerization reaction of an α-olefin in the presence of a catalyst containing a chlorine atom-containing compound (d) and a reaction solvent, wherein the chlorine atom-containing compound (d) that are at least two compounds having specific chlorine atom elimination rate is supplied in predetermined ratio.

6 Claims, 3 Drawing Sheets

(51) Int. Cl.
*C07C 2/32* (2006.01)
*C07C 11/107* (2006.01)
*B01J 31/02* (2006.01)

(52) U.S. Cl.
CPC .............. *C07C 2/32* (2013.01); *C07C 11/107* (2013.01); *B01J 2231/20* (2013.01); *C07C 2531/02* (2013.01); *C07C 2531/22* (2013.01)

(56) References Cited

U.S. PATENT DOCUMENTS

| | | | |
|---|---|---|---|
| 5,910,619 A | 6/1999 | Urata et al. | |
| 2009/0326297 A1* | 12/2009 | Emoto | B01J 31/143 585/530 |
| 2012/0302715 A1 | 11/2012 | Zilbershtein et al. | |

FOREIGN PATENT DOCUMENTS

| | | |
|---|---|---|
| CN | 102781884 A | 11/2012 |
| JP | 7-165815 | 6/1995 |
| JP | 8-134131 | 5/1996 |
| JP | 9-268136 | 10/1997 |
| JP | H10-36435 A | 2/1998 |
| JP | 2008-179631 | 8/2008 |
| JP | 2011-219474 | 11/2011 |
| JP | 2013-517938 | 5/2013 |
| JP | 2014-159391 | 9/2014 |
| WO | WO 2005/082816 A1 | 9/2005 |
| WO | WO 2011/118533 A1 | 9/2011 |

OTHER PUBLICATIONS

Written Opinion dated Jun. 28, 2016 in PCT/JP2016/059246, filed on Mar. 23, 2016.
Office Action dated Jul. 31, 2019 in Indian Patent Application No. 201717033622.
Examination Report prepared Nov. 20, 2018 and dated Dec. 11, 2018, in GCC Patent Application No. GC 2016-31060.
Office Action dated Dec. 16, 2019 in Chinese Patent Application No. 201680017280.4 (w/ computer-generated English translation).
Office Action dated Nov. 12, 2019 in Japanese Patent Application No. 2016-058887 (w/ computer-generated English translation).
GCC Examination Report attached to Official Notification dated Mar. 17, 2020 in corresponding GCC Patent Application GC No. 2016-31060.
Official Notification dated Mar. 17, 2020 in corresponding GCC Patent Application No. GC 2016-31060.

* cited by examiner

METHOD FOR PRODUCING ALPHA-OLEFIN LOW POLYMER

TECHNICAL FIELD

The present invention relates to a method for producing an α-olefin low polymer.

BACKGROUND ART

An α-olefin low polymer is usually produced by a method of subjecting an α-olefin to a low polymerization reaction in the presence of a catalyst and a reaction solvent. For example, there is disclosed a method for producing 1-hexene by a trimerization reaction of ethylene in the presence of a catalyst containing a chromium compound, a pyrrole compound, an alkylaluminum compound, and a halogen-containing compound and a reaction solvent, and as the halogen-containing compound, there are exemplified a halide of a linear hydrocarbon (Patent Document 1), a halogenated benzyl compound (Patent Document 2), and diethylaluminum chloride (Patent Document 3).

Moreover, Patent Document 4 discloses a method for producing 1-hexene by a trimerization reaction of ethylene in the presence of a catalyst containing a chromium compound, a pyrrole compound, an alkylaluminum compound, a halogen-containing compound, and further a halogenated olefin and a reaction solvent.

BACKGROUND ART DOCUMENT

Patent Document

[Patent Document 1] JP-A-8-134131
[Patent Document 2] JP-A-2011-219474
[Patent Document 3] WO2005/082816
[Patent Document 4] JP-A-2014-159391

SUMMARY OF THE INVENTION

Problems that the Invention is to Solve

In the production of the α-olefin low polymer by the low polymerization reaction of an α-olefin, there are desired a further enhancement of α-olefin low polymer selectivity and α-olefin low polymer yields and a further improvement in deterioration of catalytic activity with time.

An object of the invention is to provide a method for efficiently producing an α-olefin low polymer at a high α-olefin low polymer selectivity and a high α-olefin low polymer yield with suppressing the deterioration of catalytic activity with time, in the production of the α-olefin low polymer by the low polymerization reaction of an α-olefin.

Means for Solving the Problems

As a result of extensive and intensive studies to solve the above problems, the present inventors have found that the above problems can be solved by using, among a transition metal atom-containing compound (a), a nitrogen atom-containing compound (b), an alkylaluminum compound (c), and a chlorine atom-containing compound (d) to be used as a catalyst for the low polymerization reaction of an α-olefin, as the chlorine atom-containing compound (d), two or more compounds having different chlorine atom elimination rates relating to the reactivity to the alkylaluminum compound (c) in respective predetermined ratios.

Namely, the gist of the invention resides in the following [1] to [7].

[1]. A method for producing an α-olefin low polymer, which comprises performing a low polymerization reaction of an α-olefin in the presence of a catalyst containing a transition metal atom-containing compound (a), a nitrogen atom-containing compound (b), an alkylaluminum compound (c), and a chlorine atom-containing compound (d) and a reaction solvent, Wherein the chlorine atom-containing compound (d) contains at least two compounds selected from the group consisting of a chlorinated hydrocarbon compound and a chlorinated typical metal atom-containing compound, and the chlorine atom-containing compound (d) contains a chlorinated hydrocarbon compound as an essential component, a chlorine atom elimination rate of the chlorinated hydrocarbon compound in the chlorine atom-containing compounds (d) determined by the following measurement method are all equal to or higher than the chlorine atom elimination rate of 1,1,2,2-tetrachloroethane, the chlorine atom-containing compounds (d) containing the at least two compounds contain a first chlorine atom-containing compound (d)-1 and a second chlorine atom-containing compound (d)-2 having a chlorine atom elimination rate lower than that of the first chlorine atom-containing compound (d)-1, and the chlorine atom-containing compound (d) is supplied to the low polymerization reaction system so that the amount of the chlorine atom-containing compound (d) relative to the transition metal atom in the low polymerization reaction system becomes 2 molar equivalents or more and 50 molar equivalents or less, and the ratio of the second chlorine atom-containing compound (d)-2 to the total amount of the chlorine atom-containing compound (d) becomes 1 mol % or more and 49 mol % or less:

<Measurement Method of Chlorine Atom Elimination Rate of Chlorinated Hydrocarbon Compound>

After 15 ml of a solution obtained by diluting a measuring target chlorinated hydrocarbon compound with the reaction solvent into 0.10 mol/L is added to 60 ml of a solution obtained by diluting the alkylaluminum compound (c) with the reaction solvent into 0.15 mol/L, the whole is stirred at 80° C. for 2 hours, then remaining concentration of the measuring target chlorinated hydrocarbon compound is analyzed by a gas chromatography, and the chlorine atom elimination rate at which the chlorine atom in the measuring target chlorinated hydrocarbon compound is extracted with the alkylaluminum compound (c) is determined from the remaining amount of the measuring target chlorinated hydrocarbon compound and the reaction time.

[2] The method for producing an α-olefin low polymer according to the [1] above, wherein the first chlorine atom-containing compound (d)-1 contains a chlorinated typical metal atom-containing compound and the second chlorine atom-containing compound (d)-2 is a chlorinated hydrocarbon compound.

[3] The method for producing an α-olefin low polymer according to the [1] above, wherein both of the first chlorine atom-containing compound (d)-1 and the second chlorine atom-containing compound (d)-2 are a chlorinated hydrocarbon compound.

[4] The method for producing an α-olefin low polymer according to the [2] or [3] above, wherein the chlorine atom-containing compound (d) contains at least one of a chlorinated saturated hydrocarbon compound and a chlorinated benzyl compound.

[5] The method for producing an α-olefin low polymer according to any one of the [1] to [4] above, wherein the alkylaluminum compound (c) is triethylaluminum.

[6] The method for producing an α-olefin low polymer according to any one of the [1] to [5] above, wherein the transition metal in the transition metal atom-containing compound (a) contains chromium and the nitrogen atom-containing compound (b) contains a pyrrole compound.

[7] The method for producing an α-olefin low polymer according to any one of the [1] to [6] above, wherein the α-olefin is ethylene and the α-olefin low polymer is 1-hexene.

Effects of Invention

According to the present invention, in the production of an α-olefin low polymer by a low polymerization reaction of an α-olefin, the α-olefin low polymer can be efficiently produced at a high α-olefin low polymer selectivity and a high α-olefin low polymer yield with suppressing the deterioration of catalytic activity with time.

MODE FOR CARRYING OUT INVENTION

Figure 1:
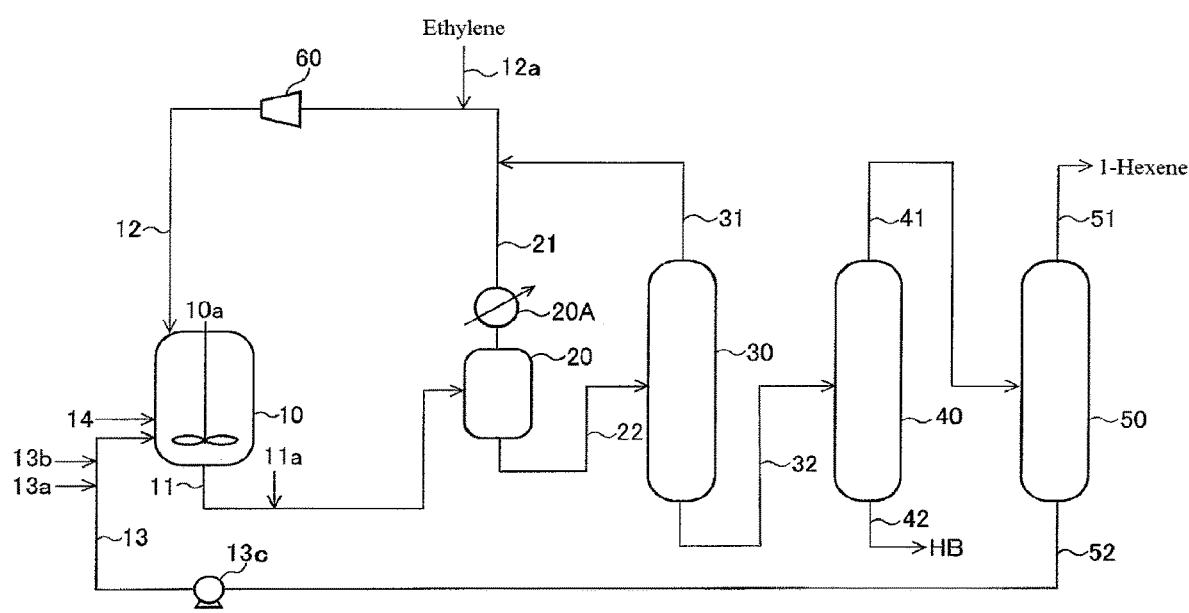
FIG. 1 is a process flow chart showing one embodiment of the method for producing an α-olefin low polymer of the invention.

The following will describe embodiments of the invention in detail. Incidentally, the invention is not limited to the following embodiments, and can be carried out with various modifications within a scope of the gist thereof.

The method for producing an α-olefin low polymer of the invention is a method for producing an α-olefin low polymer, which method comprises performing a low polymerization reaction of an α-olefin in the presence of a catalyst containing a transition metal atom-containing compound (a), a nitrogen atom-containing compound (b), an alkylaluminum compound (c), and chlorine atom-containing compounds (d) and a reaction solvent, wherein the chlorine atom-containing compounds (d) contain at least two compounds selected from the group consisting of chlorinated hydrocarbon compounds and chlorinated typical metal atom-containing compounds but the chlorine atom-containing compounds (d) contain a chlorinated hydrocarbon compound as an essential component. That is, the chlorine atom-containing compounds (d) contain at least two compounds of a chlorinated hydrocarbon compound and at least one compound selected from the group consisting of chlorinated typical metal atom-containing compounds and other chlorinated hydrocarbon compounds different from the above chlorinated hydrocarbon compound.

Chlorine atom elimination rates of the chlorinated hydrocarbon compound determined by the following measurement method are all equal to or higher than the chlorine atom elimination rate of 1,1,2,2-tetrachloroethane, and the chlorine atom-containing compounds (d) containing at least two compounds described above contain a first chlorine atom-containing compound (d)-1 and a second chlorine atom-containing compound (d)-2 having a chlorine atom elimination rate lower than that of the first chlorine atom-containing compound (d)-1.

Moreover, the chlorine atom-containing compounds (d) are supplied to the low polymerization reaction system so that the amount of the chlorine atom-containing compounds (d) to the transition metal atom in the low polymerization reaction system is 2 molar equivalents or more and 50 molar equivalents or less and the ratio of the second chlorine atom-containing compound (d)-2 to the total amount of the chlorine atom-containing compounds (d) is 1 mol % or more and 49 mol % or less.

<Measurement Method of Chlorine Atom Elimination Rate of Chlorinated Hydrocarbon Compound>

After 15 ml of a solution obtained by diluting a measuring target chlorinated hydrocarbon compound with the reaction solvent into 0.10 mol/L is added to 60 ml of a solution obtained by diluting the alkylaluminum compound (c) with the reaction solvent into 0.15 mol/L, the whole is stirred at 80° C. for 2 hours, then remaining concentration of the measuring target chlorinated hydrocarbon compound is analyzed by gas chromatography, and the chlorine atom elimination rate at which the chlorine atom in the measuring target chlorinated hydrocarbon compound is extracted with the alkylaluminum compound (c) is determined from the remaining amount of the measuring target chlorinated hydrocarbon compound and the reaction time.

Namely, the remaining amount (mol) of the measuring target chlorinated hydrocarbon compound is subtracted from the charged amount (mol) of the measuring target chlorinated hydrocarbon compound to determine an amount (mol) of the compound from which a chlorine atom is eliminated and the amount is divided by the reaction time, whereby the chlorine atom elimination rate can be calculated.

[Mechanism]

In the invention, effects of suppressing the deterioration of catalytic activity with time and enhancing the selectivity and yield of the α-olefin low polymer are obtained by using two or more compounds having chlorine atom elimination rates equal to or higher than the chlorine atom elimination rate of 1,1,2,2-tetrachloroethane as the chlorine atom-containing compounds (d) among the catalyst components and using the first chlorine atom-containing compound (d)-1 having a high chlorine atom elimination rate and the second chlorine atom-containing compound (d)-2 having a low chlorine atom elimination rate lower than the chlorine atom elimination rate of the first chlorine atom-containing compound (d)-1 in combination. Details of the mechanism are not clear but are surmised as follows.

Since the first chlorine atom-containing compound (d)-1 having a high chlorine atom elimination rate is excellent in an elimination property of a chlorine atom, the compound promptly supplies a chlorine atom in the reaction system to form a catalyst active species together with the other catalyst components. For example, in the case where the first chlorine atom-containing compound (d)-1 is hexachloroethane, it supplies a chlorine atom and itself becomes tetrachloroethylene. Incidentally, the chlorine atom elimination rate of hexachloroethane is equal to or higher than the chlorine atom elimination rate of 1,1,2,2-tetrachloroethane and the chlorine atom elimination rate of the tetrachloroethylene is lower than the chlorine atom elimination rate of 1,1,2,2-tetrachloroethane. When the catalyst active species thus formed by the supply of the chlorine atom repeats the low polymerization reaction, the active species gradually becomes a deteriorated catalyst species.

In the invention, by using the second chlorine atom-containing compound (d)-2 having a chlorine atom elimination rate lower than that of the first chlorine atom-containing compound (d)-1 in combination with the first chlorine atom-containing compound (d)-1, after the catalyst active species formed by releasing the chlorine atom from the first chlorine atom-containing compound (d)-1 becomes a deteriorated catalyst species, a chlorine atom is supplied to the deteriorated catalyst species from the second chlorine atom-containing compound (d)-2 and thus the catalyst active species is re-formed.

By thus using the second chlorine atom-containing compound (d)-2 in combination, the deteriorated catalyst species derived from the first chlorine atom-containing compound (d)-1 can be converted into the catalyst active species and thus the catalytic activity can be maintained over a long period of time. Moreover, as mentioned above, since the second chlorine atom-containing compound (d)-2 is used for acting on the catalyst species resulting from the deterioration of the catalyst active species formed by the first chlorine atom-containing compound (d)-1, it is sufficient that the amount of the second chlorine atom-containing compound (d)-2 is smaller than the amount of the first chlorine atom-containing compound (d)-1. Therefore, in the invention, the amount of the second chlorine atom-containing compound (d)-2 is 1 mol % or more and 49 mol % or less relative to the amount of the chlorine atom-containing compounds (d).

Incidentally, it is surmised that the supply of a chlorine atom is too slow in the case of a chlorine atom-containing compound having a chlorine atom elimination rate lower than that of 1,1,2,2-tetrachloroethane and thus the above-described improving effects are small. Therefore, in the invention, as the chlorine atom-containing compounds (d), two or more compounds having chlorine atom elimination rates equal to or higher than the chlorine atom elimination rate of 1,1,2,2-tetrachloroethane are used.

Namely, those having a chlorine atom elimination rate lower than the chlorine atom elimination rate of 1,1,2,2-tetrachloroethane are not included in the chlorine atom-containing compounds (d) in the invention. For example, the aforementioned hexachloroethane supplies a chlorine atom to become tetrachloroethylene but, since the chlorine atom elimination rate of tetrachloroethylene is lower than the chlorine atom elimination rate of 1,1,2,2-tetrachloroethane, tetrachloroethylene is not included in the chlorine atom-containing compounds (d) in the invention.

The measurement method of the chlorine atom elimination rate of the chlorinated hydrocarbon compound in the invention includes determination of the chlorine atom elimination rate of a chlorine atom based on the decomposition rate of the chlorinated hydrocarbon compound by the reaction of the chlorinated hydrocarbon compound with the alkylaluminum compound (c). For example, the chlorine atom of the chlorinated hydrocarbon compound coordinates to a vacant orbital of triethylaluminum that is a Lewis acid and thereafter the chlorine atom is eliminated. The rate at that time is evaluated.

Moreover, the strength of a chemical bond is represented by bond energy between atoms and is as follows: Covalent bond>Ionic bond. Accordingly, the chlorine atom elimination rate by the above reaction is defined as follows: [Chlorinated typical metal atom-containing compound]>[Chlorinated hydrocarbon compound]. That is, in the case where a chlorinated typical metal atom-containing compound and a chlorinated hydrocarbon compound are contained as the chlorine atom-containing compounds (d), the chlorinated typical metal atom-containing compound is included in the first chlorine atom-containing compound (d)-1 and thus it is not necessary to measure the chlorine atom elimination rate of the chlorinated typical metal atom-containing compound.

Moreover, as mentioned later, in the case where three or more compounds are contained as the chlorine atom-containing compounds (d), a chlorine atom-containing compound having the lowest chlorine atom elimination rate is taken as the compound (d)-2 and all of the compounds each having a chlorine atom elimination rate higher than the chlorine atom elimination rate are taken as the compounds (d)-1. Therefore, even in the case where two or more chlorinated typical metal atom-containing compounds and one or more chlorinated hydrocarbon compounds are contained as the chlorine atom-containing compounds (d), the two or more chlorinated typical metal atom-containing compounds are all the first chlorine atom-containing compounds (d)-1 and a chlorine atom-containing compound having the lowest chlorine atom elimination rate is the second chlorine atom-containing compound (d)-2, so that it is not necessary to measure the chlorine atom elimination rates of the chlorinated typical metal atom-containing compounds also in this case.

Therefore, a chlorinated typical metal atom-containing compound is used as the first chlorine atom-containing compound (d)-1 and a chlorinated hydrocarbon compound is used as the second chlorine atom-containing compound (d)-2 or, in a case of using two or more of chlorinated hydrocarbon compounds having different chlorine atom elimination rates, the chlorine atom elimination rate is determined according to the above measurement method of the chlorine atom elimination rate of the chlorinated hydrocarbon compound and the one having the lowest chlorine atom elimination rate may be taken as the second chlorine atom-containing compound (d)-2, and the other compound(s) may be taken as the first chlorine atom-containing compound (d)-1.

In the above measurement method of the chlorine atom elimination rate, as the reaction solvent, it is preferred to use the same solvent as the reaction solvent (dehydrated one) to be used in the low polymerization reaction but they are not necessarily the same and one or two or more selected from the reaction solvents to be mentioned later may be used.

Moreover, as the alkylaluminum compound (c) to be used in the above measurement method of the chlorine atom elimination rate, it is preferred to use the same compound as the alkylaluminum compound (c) to be used in the low polymerization reaction but they are not necessarily the same and one or two or more selected from the examples of the alkylaluminum compound (c) to be mentioned later may be used. Since the alkylaluminum compound (c) easily reacts with oxygen and water in the air to change in the form, the compound is handled under an atmosphere of an inert gas such as nitrogen or argon substantially containing no oxygen and water, including the period of the reaction.

Incidentally, the reaction temperature in the measurement of the chlorine atom elimination rate is controlled to 80° C. However, in a case where the difference in the chlorine atom elimination rate is difficult to judge for the chlorine atom-containing compounds to be measured, it is possible to perform the measurement with changing the temperature. In that case, the measurement may be performed with lowering the temperature to 50° C., or elevating the temperature to 140° C.

Furthermore, in the measurement of the chlorine atom elimination rate, in the case where there is a concern that the chlorine atom-containing compound, the alkylaluminum compound (c), and/or the solvent are vaporized to outside of the reactor, a tightly closed reactor is used.

The difference in the chlorine atom elimination rate of compounds is judged under the same reaction conditions (temperature, time, molar concentration, alkylaluminum compound (c), solvent, rotation number for stirring, and the like).

(Raw Material α-Olefin)

In the method for producing an α-olefin low polymer of the invention, as the α-olefin to be used as a raw material, for example, a substituted or unsubstituted α-olefin having 2 to 8 carbon atoms is mentioned. Specific examples of such an α-olefin include ethylene, propylene, 1-butene, 1-hexene, 1-octene, 3-methyl-1-butene, and 4-methyl-1-pentene. Of these, ethylene is suitable as the raw material α-olefin of the invention.

The α-olefin as a raw material may be used alone or a plurality thereof may be used.

(α-Olefin Low Polymer)

The α-olefin low polymer to be produced in the invention means one obtained by subjecting the raw material α-olefin to a low polymerization reaction. The low polymerization reaction of the α-olefin means oligomerization of the raw material α-olefin.

The α-olefin low polymer means an oligomer in which several molecules of the raw material α-olefin are bonded. The α-olefin low polymer to be obtained may be one kind thereof or may be a mixture containing two or more kinds thereof.

Specifically, it means an oligomer in which 2 to 10 molecules, preferably 2 to 5 molecules of the α-olefin that is a raw material are bonded. In the case where ethylene is used as a raw material, as the α-olefin low polymer that is an objective product, a substituted or unsubstituted linear or branched α-olefin having 4 to 10 carbon atoms is preferred and a unsubstituted linear α-olefin having 4 to 10 carbon atoms is more preferred. Specifically, there may be mentioned 1-butene that is a dimmer of ethylene, 1-hexene that is a trimer, 1-octene that is a tetramer, 1-decene that is a pentamer, and the like, 1-hexene or 1-octene is preferred, and 1-hexene is more preferred. In the case where the objective product is 1-hexene, the content of 1-hexene in a mixture of products is preferably 90% by weight or more.

Moreover, in the case of using ethylene as a raw material, it is desired to use highly pure ethylene of 99.9 mol % or more but impurity components other than ethylene may be contained in the raw material. As specific impurity components, there may be mentioned methane, ethane, nitrogen, propane, propylene, propadiene, 1,3-butadiene, methanol, propanol, hydrogen, oxygen, water, acetylene, carbon dioxide, carbon monoxide, hydrogen sulfide, carbonyl sulfide, arsine, oils, nitrogen-containing compounds, carbonyl compounds, oxygen-containing compounds, chlorine-containing compounds, and the like.

As for methane, ethane, and nitrogen, the content is preferably 0.1 mol % or less relative to raw material ethylene and, as for propane and propylene, the content is preferably 10 mol ppm or less relative to raw material ethylene.

As for propadiene, 1,3-butadiene, methanol, propanol, hydrogen, oxygen, water, acetylene, carbon dioxide, arsine, oils, nitrogen-containing compounds, carbonyl compounds, oxygen-containing compounds, chlorine-containing compounds, and phosphorus-containing compounds, in order to prevent the poisoning of the catalyst, the content is preferably 5 mol ppm or less and further preferably 1 mol ppm or less relative to raw material ethylene.

Since it is considered that carbon monoxide, hydrogen sulfide, and carbonyl sulfide strongly poison the catalyst, the content is preferably 1 mol ppm or less and further preferably 0.2 mol ppm or less relative to raw material ethylene.

(Catalyst)

The catalyst to be used in the invention contains a transition metal atom-containing compound (a), a nitrogen atom-containing compound (b), an alkylaluminum compound (c), and chlorine atom-containing compounds (d).

<Transition Metal Atom-Containing Compound (a)>

The metal contained in the transition metal atom-containing compound (a) (hereinafter sometimes referred to as "catalyst component (a)") to be suitably used as a constituting component of the catalyst of the invention is not particularly limited so long as it is a transition metal. Especially, a transition metal belonging to 4 to 6 groups of the periodic table is preferably used. Specifically, it is preferably at least one metal selected from the group consisting of chromium, titanium, zirconium, vanadium, and hafnium. Further preferred is chromium or titanium and most preferred is chromium.

The transition metal atom-containing compound (a) is usually at least one compound represented by the general formula: $MeZ_n$. Here, in the general formula: $MeZ_n$, Me represents a transition metal element and Z represents any organic group or inorganic group or an electronegative atom. n represents an integer of 1 to 6 and is preferably 2 or more. In the case where n is 2 or more, Z may be the same or different from each other.

As the organic group, there may be mentioned an organic group containing a hydrocarbon group having 1 to 30 carbon atoms, which may have a substituent. Specifically, there may be mentioned a carbonyl group, an alkoxy group, a carboxyl group, a β-diketonate group, a β-ketocarboxyl group, a β-ketoester group, an amido group, and the like.

As the inorganic group, metal salt-forming groups such as a nitric acid group and a sulfuric acid group may be mentioned.

As the electronegative atom, oxygen, halogen, and the like may be mentioned. Incidentally, transition metal atom-containing compounds (a) containing halogen are not included in the chlorine atom-containing compounds (d) to be mentioned later.

In the case of the transition metal atom-containing compound (a) in which the transition metal is chromium (hereinafter sometimes referred to as "chromium-containing compound"), specific examples thereof include chromium (IV)-tert-butoxide, chromium(III) acetylacetonate, chromium(III) trifluoroacetylacetonate, chromium(III) hexafluoroacetylacetonate, chromium(III) (2,2,6,6-tetramethyl-3,5-heptanedionate), $Cr(PhCOCHCOPh)_3$ (where Ph represents a phenyl group), chromium(II) acetate, chromium(III) acetate, chromium(III) 2-ethylhexanoate, chromium(III) benzoate, chromium(III) naphthenate, chromium(III) heptanoate, $Cr(CH_3COCHCOOCH_3)_3$, chromous chloride, chromic chloride, chromous bromide, chromic bromide, chromous iodide, chromic iodide, chromous fluoride, and chromic fluoride.

In the case of the transition metal atom-containing compound (a) in which the transition metal is titanium (hereinafter sometimes referred to as "titanium-containing compound"), specific examples thereof include $TiCl_4$, $TiBr_4$, $TiBr_4$, $TiBrCl_3$, $TiBr_2Cl_2$, $Ti(OC_2H_5)_4$, $Ti(OC_2H_5)_2Cl_2$, $Ti(O-n-C_3H_7)_4$, $Ti(O-n-C_3H_7)_2Cl_2$, $Ti(O-iso-C_3H_7)_4$, $Ti(O-iso-C_3H_7)_2Cl_2$, $Ti(O-n-C_4H_9)_4$, $Ti(O-n-C_4H_9)_2Cl_2$, $Ti(O-iso-C_4H_9)_4$, $Ti(O-iso-C_4H_9)_2Cl_2$, $Ti(O-tert-C_4H_9)_4$, $Ti(O-tert-C_4H_9)_2Cl_2$, $TiCl_4(thf)_2$ (in the chemical formula described in the left, thf represents tetrahydrofuran), Ti(($CH_3$)$_2$N)$_4$, Ti(($C_2H_5$)$_2$N)$_4$, Ti((n-$C_3H_7$)$_2$N)$_4$, Ti((iso-$C_3H_7$)$_2$N)$_4$, Ti((n-$C_4H_9$)$_2$N)$_4$, Ti((tert-$C_4H_9$)$_2$N)$_4$, Ti($OSO_3CH_3$)$_4$, Ti($OSO_3C_2H_5$)$_4$, Ti($OSO_3C_3H_7$)$_4$, Ti($OSO_3C_4H_9$)$_4$, TiCp$_2$Cl$_2$, TiCp$_2$ClBr (in the chemical formula described in the left, Cp represents a cyclopentadienyl group; the same shall apply in the following zirconium-containing compounds), Ti($OCOC_2H_5$)$_4$, Ti($OCOC_2H_5$)$_2$Cl$_2$, Ti($OCOC_3H_7$)$_4$, Ti($OCOC_3H_7$)$_2$Cl$_2$, Ti($OCOC_3H_7$)$_4$, Ti($OCOC_3H_7$)$_2$Cl$_2$, Ti($OCOC_4H_9$)$_4$, and Ti($OCOC_4H_9$)$_2$Cl$_2$.

In the case of the transition metal atom-containing compound (a) in which the transition metal is zirconium (hereinafter sometimes referred to as "zirconium-containing compound"), specific examples thereof include ZrCl$_4$, ZrBr$_4$, ZrI$_4$, ZrBrCl$_3$, ZrBr$_2$Cl$_2$, Zr($OC_2H_5$)$_4$, Zr($OC_2H_5$)$_2$Cl$_2$, Zr(O-n-$C_3H_7$)$_4$, Zr(O-n-$C_3H_7$)$_2$Cl$_2$, Zr(O-iso-$C_3H_7$)$_4$, Zr(O-iso-$C_3H_7$)$_2$Cl$_2$, Zr(O-n-$C_4H_9$)$_4$, Zr(O-n-$C_4H_9$)$_2$Cl$_2$, Zr(O-iso-$C_4H_9$)$_4$, Zr(O-iso-$C_4H_9$)$_2$Cl$_2$, Zr(O-tert-$C_4H_9$)$_4$, Zr(O-tert-$C_4H_9$)$_2$Cl$_2$, Zr(($CH_3$)$_2$N)$_4$, Zr(($C_2H_5$)$_2$N)$_4$, Zr((n-$C_3H_7$)$_2$N)$_4$, Zr((iso-$C_3H_7$)$_2$N)$_4$, Zr((n-$C_4H_9$)$_2$N)$_4$, Zr((tert-$C_4H_9$)$_2$N)$_4$, Zr($OSO_3CH_3$)$_4$, Zr($OSO_3C_2H_5$)$_4$, Zr($OSO_3C_3H_7$)$_4$, Zr($OSO_3C_4H_9$)$_4$, ZrCp$_2$Cl$_2$, ZrCp$_2$CkBr, Zr($OCOC_2H_5$)$_4$, Zr($OCOC_2H_5$)$_2$Cl$_2$, Zr($OCOC_3H_7$)$_4$, Zr($OCOC_3H_7$)$_2$Cl$_2$, Zr($OCOC_3H_7$)$_4$, Zr($OCOC_3H_7$)$_2$Cl$_2$, Zr($OCOC_4H_9$)$_4$, Zr($OCOC_4H_9$)$_2$Cl$_2$, ZrCl$_2$(HCOCFCOF)$_2$, and ZrCl$_2$($CH_3$COCFCOCH$_3$)$_2$.

In the case of the transition metal atom-containing compound (a) in which the transition metal is hafnium (hereinafter sometimes referred to as "hafnium-containing compound"), specific examples thereof include dimethylsilylenebis{1-(2-methyl-4-isopropyl-4H-azulenyl)}hafnium dichloride, dimethylsilylenebis{1-(2-methyl-4-phenyl-4H-azulenyl)}hafnium dichloride, dimethylsilylenebis[1-{2-methyl-4-(4-chlorophenyl)-4H-azulenyl}]hafnium dichloride, dimethylsilylenebis[1-{2-methyl-4-(4-fluorophenyl)-4H-azulenyl}]hafnium dichloride, dimethylsilylenebis[1-{2-methyl-4-(3-chlorophenyl)-4H-azulenyl}]hafnium dichloride, dimethylsilylenebis[1-{2-methyl-4-(2,6-dimethylphenyl)-4H-azulenyl}]hafnium dichloride, dimethylsilylenebis{1-(2-methyl-4,6-diisopropyl-4H-azulenyl)}hafnium dichloride, diphenylsilylenebis{1-(2-methyl-4-phenyl-4H-azulenyl)}hafnium dichloride, methylphenylsilylenebis{1-(2-methyl-4-phenyl-4H-azulenyl)}hafnium dichloride, methylphenylsilylenebis[1-{2-methyl-4-(1-naphthyl)-4H-azulenyl}]hafnium dichloride, dimethylsilylenebis{1-(2-ethyl-4-phenyl-4H-azulenyl)}hafnium dichloride, dimethylsilylenebis[1-{2-ethyl-4-(1-anthracenyl)-4H-azulenyl}]hafnium dichloride, dimethylsilylenebis[1-{2-ethyl-4-(2-anthracenyl)-4H-azulenyl}]hafnium dichloride, dimethylsilylenebis[1-{2-ethyl-4-(9-phenanthryl)-4H-azulenyl}]hafnium dichloride, dimethylmethylenebis[1-{2-methyl-4-(4-biphenylyl)-4H-azulenyl}]hafnium dichloride, dimethylgermylenebis[1-{2-methyl-4-(4-biphenylyl)-4H-azulenyl}]hafnium dichloride, dimethylsilylenebis[1-{2-ethyl-4-(3,5-dimethyl-4-trimethylsilylphenyl)-4H-azulenyl}]hafnium dichloride, dimethylsilylene[1-{2-methyl-4-(4-biphenylyl)-4H-azulenyl}][1-{2-methyl-4-(4-biphenylyl)indenyl}]hafnium dichloride, dimethylsilylene {1-(2-ethyl-4-phenyl-4H-azulenyl)}{1-(2-methyl-4,5-benzoindenyl)}hafnium dichloride, dimethylsilylenebis{1-(2-methyl-4-phenylindenyl)}hafnium dichloride, dimethylsilylenebis{1-(2-methyl-4,5-benzoindenyl)}hafnium dichloride, and dimethylsilylenebis[1-{2-methyl-4-(1-naphthyl)indenyl}]hafnium dichloride.

These transition metal atom-containing compounds (a) may be used alone as a single compound or two or more thereof may be used in combination.

Of these transition metal atom-containing compounds (a), chromium-containing compounds are preferred and, of the chromium-containing compounds, particularly preferred is chromium(III) 2-ethylhexanoate.

<Nitrogen Atom-Containing Compound (b)>

In the invention, the nitrogen atom-containing compound (b) (hereinafter sometimes referred to as "catalyst component (b)") to be suitably used as a constituting component of the catalyst in the invention is not particularly limited but amines, amides, or imides may be mentioned.

As the amines, for example, a pyrrole compound and an indole compound may be mentioned. Specific examples of the pyrrole compound include pyrrole, an alkylpyrrole such as 2,4-dimethylpyrrole, 2,5-dimethylpyrrole, 2,5-diethylpyrrole, 2,4-diethylpyrrole, 2,5-di-n-propylpyrrole, 2,5-di-n-butylpyrrole, 2,5-di-n-pentylpyrrole, 2,5-di-n-hexylpyrrole, 2,5-dibenzylpyrrole, 2,5-diisopropylpyrrole, 2-methyl-5-ethylpyrrole, 2,5-dimethyl-3-ethylpyrrole, 3,4-dimethylpyrrole, a halogenated pyrrole such as 3,4-dichloropyrrole, 2,3,4,5-tetrachloropyrrole, an acetylpyrrole such as 2-acetylpyrrole, and a dipyrrole having two pyrrole rings bonded through a substituent, and derivatives thereof. Specific examples of the indole compound include indole, and an alkylindole such as 2-methylindole.

Examples of the derivatives include metal pyrrolide derivatives. Specific examples thereof include aluminum pyrrolides such as diethylaluminum pyrrolide, ethylaluminum dipyrrolide, aluminum tripyrrolide, diethylaluminum (2,5-dimethylpyrrolide), ethylaluminum bis(2,5-dimethylpyrrolide), aluminum tris(2,5-dimethylpyrrolide), diethyl aluminum (2,5-diethylpyrrolide), ethylaluminum bis(2,5-diethylpyrrolide), and aluminum tris(2,5-diethylpyrrolide), sodium pyrrolides such as sodium pyrrolide and sodium (2,5-dimethylpyrrolide), lithium pyrrolides such as lithium pyrrolide and lithium (2,5-dimethylpyrrolide), and potassium pyrrolides such as potassium pyrrolide and potassium (2,5-dimethylpyrrolide). Incidentally, the aluminum pyrrolides are not included in the alkylaluminum compound (c) to be mentioned later. Furthermore, the halogen-containing pyrrole compounds are not included in the chlorine atom-containing compounds (d) to be mentioned later.

Moreover, there may be used diphosphinoamines such as bis(diethylphosphino-ethyl)amine, bis(diphenylphosphino-ethyl)amine, N,N-bis(diphenylphosphino)methylamine, N,N-bis(diphenylphosphino)isopropylamine, and N,N-bis(diphenylphosphino)-1,2-dimethylpropylamine.

Examples of the amides include acetamide, N-methylhexanamide, succinamide, maleamide, N-methylbenzamide, imidazole-2-carboxamide, di-2-thenoylamine, β-lactam, δ-lactam, and ε-caprolactam, or salts of them with a metal belonging to 1, 2, or 13 group of the periodic table.

Examples of the imides include 1,2-cyclohexanedicarboxyimide, succinimide, phthalimide, maleimide, 2,4,6-piperidinetrione, and perhydroazecine-2,10-dione, or salts of them with a metal belonging to 1, 2, or 13 group of the periodic table.

Examples of sulfonamides and sulfonimides include benzenesulfonamide, N-methylmethanesulfonamide, and N-methyltrifluoromethylsulfonamide, or salts of them with a metal belonging to 1, 2, or 13 group of the periodic table.

These nitrogen atom-containing compounds (b) may be used alone as a single compound or two or more thereof may be used in combination.

In the invention, of these, an amine is preferred. In particular, a pyrrole compound is more preferred and particularly preferred is 2,5-dimethylpyrrole or diethylaluminum (2,5-dimethylpyrrolide).

<Alkylaluminum Compound (c)>

The alkylaluminum compound (c) (hereinafter sometimes referred to as "catalyst component (c)") to be suitably used as a constituting component of the catalyst of the invention is not particularly limited but there may be mentioned a trialkylaluminum compound, an alkoxyalkylaluminum compound, a hydrogenated alkylaluminum compound, and an alkylaluminoxane compound.

Incidentally, the chlorinated alkylaluminum compound is not included in the alkylaluminum compound (c) and is included in the chlorine atom-containing compounds (d) to be mentioned later.

As the trialkylaluminum compound, the trialkylaluminum compound where one alkyl group therein has 1 to 8 carbon atom may be mentioned, and for example, trimethylaluminum, triethylaluminum, and triisobutylaluminum may be mentioned. As the alkoxyaluminum compound, for example, diethylaluminum ethoxide may be mentioned. As the hydrogenated alkylaluminum compound, for example, diethylaluminum hydride may be mentioned. As the alkylaluminoxane compound, for example, methylaluminoxane may be mentioned.

These alkylaluminum compounds (c) may be used alone as a single compound or two or more thereof may be used in combination.

Of these, a trialkylaluminum compound is preferred and triethylaluminum is further preferred.

<Chlorine Atom-Containing Compounds (d)>

In the invention, as the chlorine atom-containing compounds (d) (hereinafter sometimes referred to as "catalyst component (d)"), totally at least two compounds of a chlorinated hydrocarbon compound and at least one compound selected from chlorinated typical metal atom-containing compounds and the other chlorinated hydrocarbon compounds are preferred.

Of these, as the chlorinated typical metal atom-containing compounds, a chlorine compound containing a typical metal belonging to 12 to 15 groups of the periodic table may be mentioned, specially, there may be mentioned diethylaluminum chloride, ethylaluminum sesquichloride, ethylaluminum dichloride, aluminum trichloride, ethylaluminum ethoxy chloride, tin(II) chloride, tin(IV) chloride, germanium tetrachloride, antimony (111) chloride, antimony (V) chloride, zinc chloride, and the like.

The chlorinated hydrocarbon compound has a chlorine atom elimination rate equal to or higher than that of 1,1,2,2-tetrachloroethane, and specially, as the chlorinated hydrocarbon compound, there may be mentioned carbon tetrachloride, allyl chloride, chlorinated saturated hydrocarbon compounds, chlorinated benzyl compounds, and chlorinated aromatic polycyclic compounds. Of these, it is preferred to incorporate at least either one of the chlorinated saturated hydrocarbon compound and the chlorinated benzyl compound from the viewpoint of improving a selectivity of α-olefin low polymer in a low polymerization reaction of α-olefin, and the number of carbon atoms of the chlorinated saturated hydrocarbon compound is preferably 2 or more and 10 or less.

As the chlorinated saturated hydrocarbon compound having 2 or more and 10 or less of carbon atoms, 1,1,2,2-tetrachloroethane, pentachloroethane, hexachloroethane, and the like may be mentioned.

As the cholorinated benzyl compound, there may be mentioned benzyl chloride, (1-chloroethyl)benzene, 2-methylbenzyl chloride, 3-methylbenzyl chloride, 4-methylbenzyl chloride, 4-ethylbenzyl chloride, 4-isopropylbenzyl chloride, 4-tert-butylbenzyl chloride, 4-vinylbenzyl chloride, α-ethyl-4-methylbenzyl chloride, α,α'-dichloro-o-xylene, α,α'-dichloro-m-xylene, α,α'-dichloro-p-xylene, 2,4-dimethylbenzyl chloride, 2,5-dimethylbenzyl chloride, 2,6-dimethylbenzyl chloride, 3,4-dimethylbenzyl chloride, 2,4,5-trimethylbenzyl chloride, 2,4,6-trim ethyl benzyl chloride, 2,4,6-triisopropylbenzyl chloride, 2,3,5,6-tetramethylbenzyl chloride, 2-chlorobenzyl chloride, 3-chlorobenzyl chloride, 4-chlorobenzyl chloride, 2-bromobenzyl chloride, 3-bromobenzyl chloride, 4-bromobenzyl chloride, 2-fluorobenzyl chloride, 3-fluorobenzyl chloride, 4-fluorobenzyl chloride, 2-nitrobenzyl chloride, 3-nitrobenzyl chloride, 4-nitrobenzyl chloride, 2-cyanobenzyl chloride, 3-cyanobenzyl chloride, 4-cyanobenzyl chloride, 2-methoxybenzyl chloride, 3-methoxybenzyl chloride, 4-methoxybenzyl chloride, 2-phenoxybenzyl chloride, 4-(methylthio)benzyl chloride, 4-(trifluoromethoxy)benzyl chloride, 1-(1-chloroethyl)-4-nitrobenzene, 2,3-dichlorobenzyl chloride, 2,4-dichlorobenzyl chloride, 2,6-dichlorobenzyl chloride, 3,4-dichlorobenzyl chloride, 2,4-difluorobenzyl chloride, 2,6-difluorobenzyl chloride, 2-chloro-4-fluorobenzyl chloride, 2-chloro-6-fluorobenzyl chloride, 4-bromo-2-fluorobenzyl chloride, 2-methyl-3-nitrobenzyl chloride, 4-methyl-3-nitrobenzyl chloride, 5-methyl-2-nitrobenzyl chloride, 2-methyl-2-phenoxybenzyl chloride, α,α',2,3,5,6-hexachloro-p-xylene, α,α',2,4,5,6-hexachloro-m-xylene, and the like.

Moreover, as the chlorinated aromatic polycyclic compounds, there may be 1,4-bis-chloromethyl-2,3-dimethylnaphthalene, 1,8-bis-chloromethyl-2,3,4,5,6,7-hexamethylnaphthalene, 9-(chloromethyl)anthracene, 9,10-bis(chloromethyl)anthracene, 7-(chloromethyl)benzanthracene, 7-chloromethyl-12-methylbenzanthracene, and the like.

In the invention, it is a characteristic feature that, as the chlorine atom-containing compounds (d), there are used at least two compounds in which the chlorine atom elimination rates mentioned above are equal to or higher than the chlorine atom elimination rate of 1,1,2,2-tetrachloroethane and the chlorine atom elimination rates are different from each other. Moreover, it is another characteristic feature that, among these, one kind or more of the compounds having a higher chlorine atom elimination rate are taken as the first chlorine atom-containing compound (d)-1, the compound having the lowest chlorine atom elimination rate is taken as the second chlorine atom-containing compound (d)-2 and these compounds are used in predetermined ratios as mentioned later.

As the chlorine atom-containing compound having a chlorine atom elimination rate lower than the chlorine atom elimination rate of 1,1,2,2-tetrachloroethane, for example, there may be mentioned chlorobutane, 1,2-dichloroethane, 1,2-dichloroethylene, trichloroethylene, tetrachloroethylene (perchloroethylene), and the like. They are not included in the chlorinated hydrocarbon compounds that are the chlorine atom-containing compounds (d) in the invention.

As a combination of the first chlorine atom-containing compound (d)-1 and the second chlorine atom-containing compound (d)-2, there may be, for example, mentioned embodiments such as a combination of a chlorinated typical metal atom-containing compound and a chlorinated hydrocarbon compound and a combination of a chlorinated hydrocarbon compound and another chlorinated hydrocarbon compound.

In a case of containing two kinds of the chlorine atom-containing compounds (d), the following will exemplify combinations of specific compounds and they are exemplified in the order of the first chlorine atom-containing compound (d)-1+the second chlorine atom-containing compound (d)-2.

<Combination of Chlorinated Typical Metal Atom-Containing Compound and Chlorinated Hydrocarbon Compound>
  diethylaluminum chloride+hexachloroethane
  diethylaluminum chloride+1,1,2,2-tetrachloroethane
  diethylaluminum chloride+benzyl chloride
  tin(IV) chloride+hexachloroethane
  tin(IV) chloride+1,1,2,2-tetrachloroethane
  tin(IV) chloride+benzyl chloride
  germanium tetrachloride+hexachloroethane
  germanium tetrachloride+1,1,2,2-tetrachloroethane
  germanium tetrachloride+benzyl chloride
  antimony(III) chloride+hexachloroethane
  antimony(III) chloride+1,1,2,2-tetrachloroethane
  antimony(III) chloride+benzyl chloride <Combination of Chlorinated Hydrocarbon Compound and Chlorinated Hydrocarbon Compound>
  benzyl chloride+allyl chloride
  benzyl chloride+hexachloroethane
  benzyl chloride+1,1,2,2-tetrachloroethane
  allyl chloride+hexachloroethane
  allyl chloride+1,1,2,2-tetrachloroethane
  hexachloroethane+1,1,2,2-tetrachloroethane As described above, the compounds are not always specified to either one of the first chlorine atom-containing compound (d)-1 and the second chlorine atom-containing compound (d)-2 and, as the cases of benzyl chloride and hexachloroethane, there are compounds which may be not only the first chlorine atom-containing compound (d)-1 but also the second chlorine atom-containing compound (d)-2 depending on the other chlorine atom-containing compound to be combined.

Incidentally, in the case where three or more kinds of compounds each having a chlorine atom elimination rate equal to or higher than the chlorine atom elimination rate of 1,1,2,2-tetrachloroethane, i.e., the chlorine atom-containing compounds (d), a chlorine atom-containing compound having the lowest chlorine atom elimination rate is taken as the compound (d)-2 and all of the compounds each having a chlorine atom elimination rate higher than the chlorine atom elimination rate are taken as the compounds (d)-1. Therefore, the ratio of the amount of the first chlorine atom-containing compounds (d)-1 in the chlorine atom-containing compounds (d) becomes a ratio of the sum of the chlorine atom-containing compounds other than the second chlorine atom-containing compound (d)-2 having the lowest chlorine atom elimination rate.

For example, in the case where the chlorine atom-containing compounds (d) are three compounds of benzyl chloride, hexachloroethane, and ally chloride, benzyl chloride and allyl chloride are the first chlorine atom-containing compounds (d)-1 and hexachloroethane is the second chlorine atom-containing compound (d)-2.

<Supply Amount of Catalyst Components>

The ratios of individual constituting components, i.e., the transition metal atom-containing compound (a), the nitrogen atom-containing compound (b), the alkylaluminum compound (c), and the chlorine atom-containing compounds (d) are not particularly limited but are usually, relative to 1 mol of the transition metal atom-containing compound (a), from 1 mol to 50 mol, preferably from 2 mol to 30 mol of the nitrogen atom-containing compound (b), and from 1 mol to 200 mol, preferably from 10 mol to 150 mol of the alkylaluminum compound (c). Moreover, a lower limit of the chlorine atom-containing compounds (d) (total of the first chlorine atom-containing compound (d)-1 and the second chlorine atom-containing compound (d)-2) is usually 2 mol, preferably 3 mol, and further preferably 4 mol and an upper limit thereof is usually 50 mol, preferably 30 mol, more preferably 25 mol, and further preferably 20 mol, relative to 1 mol of the transition metal atom-containing compound (a). Incidentally, the number of mol relative to 1 mol of the transition metal atom-containing compound (a) has the same meaning as the molar equivalent to the transition metal atom in the low polymerization reaction system.

In the invention, the chlorine atom-containing compounds (d) are supplied to the reaction system so that the molar ratio of the second chlorine atom-containing compound (d)-2 to the chlorine atom-containing compounds (d) (total of the first chlorine atom-containing compound (d)-1 and the second chlorine atom-containing compound (d)-2) becomes usually from 1% to 49%, preferably from 2% to 45%, and further preferably from 4% to 40%.

When the supply amount of the chlorine atom-containing compounds (d) is larger than the above upper limit, the coordination of the chlorine atom to the catalyst active species becomes excessive and the coordination of the α-olefin that is a raw material is inhibited, so that there is a concern that reaction activity decreases. Moreover, when the supply amount of the chlorine atom-containing compounds (d) is lower than the above lower limit, the catalyst active species after the initiation of the reaction is insufficient as described above and there is a concern that the reaction activity decreases.

When the second chlorine atom-containing compound (d)-2 is more than the above upper limit, there is a concern that the reaction activity decreases. When it is less than the above lower limit, as described above, there is a concern that the transformation of the catalyst active species formed with the first chlorine atom-containing compound (d)-1 into the deteriorated catalyst species cannot be suppressed. That is, by controlling the content of the chlorine atom-containing compounds (d) and the contents of the first chlorine atom-containing compound (d)-1 and the second chlorine atom-containing compound (d)-2 to the above-described ranges, the functions of individual compounds can be satisfactorily exhibited.

The first chlorine atom-containing compound (d)-1 and the second chlorine atom-containing compound (d)-2 are preferably supplied so that the first chlorine atom-containing compound (d)-1 becomes from 1.5 to 25.5 molar equivalents and the second chlorine atom-containing compound (d)-2 becomes from 0.1 to 24.5 molar equivalents to the transition metal atom in the reaction system, further preferably supplied so that the first chlorine atom-containing compound (d)-1 becomes from 2.5 to 16.5 molar equivalents and the second chlorine atom-containing compound (d)-2 becomes from 0.2 to 13.5 molar equivalents to the transition metal atom in the reaction system, especially preferably supplied so that the first chlorine atom-containing compound (d)-1 becomes from 3.5 to 14.0 molar equivalents and the second chlorine atom-containing compound (d)-2 becomes from 0.3 to 11.0 molar equivalents to the transition metal atom in the reaction system.

In the invention, the amount of the catalyst composed of the catalyst components (a) to (d) to be used is not particularly limited but is usually an amount so as to be from $1.0 \times 10^{-7}$ mol to 0.5 mol, preferably from $5.0 \times 10^{-7}$ mol to 0.2 mol, and further preferably from $1.0 \times 10^{-6}$ mol to 0.05 mol in terms of the transition metal element of the transition metal atom-containing compound (a), per 1 liter of the reaction solvent to be mentioned later.

<Method for Supplying Catalyst Components>

In the invention, in the case of using ethylene as the α-olefin (raw material α-olefin), it is preferred to use a chromium-containing compound as the transition metal atom-containing compound (a) and bring ethylene into contact with the chromium-containing compound that is a transition metal atom-containing compound (a) in a mode where the transition metal atom-containing compound (a) does not come into contact with the alkylaluminum compound (c) beforehand.

By adopting such a contact mode, the trimerization reaction of ethylene can be selectively carried out and 1-hexene that is a trimer of ethylene can be obtained from raw material ethylene in a selectivity of 90% or more. Furthermore, in this case, the ratio of 1-hexene in hexenes can be increased to 99% or more.

Here, the "mode where the transition metal atom-containing compound (a) does not come into contact with the alkylaluminum compound (c) beforehand" means that such a mode is maintained not only at the starting time of the low polymerization reaction of ethylene but also even at subsequent additional supply of ethylene and catalyst components to the reactor. Moreover, also in the case of a batch reaction type, it is desirable to utilize the same mode.

As contact modes in the above continuous reaction type, the following (1) to (9) may be mentioned:
(1) a method of simultaneously introducing a mixture of the catalyst components (a), (b), and (d) and the catalyst component (c) into the reactor, separately;
(2) a method of simultaneously introducing a mixture of the catalyst components (b) to (d) and the catalyst component (a) into the reactor, separately;
(3) a method of simultaneously introducing a mixture of the catalyst components (a) and (b) and a mixture of the catalyst components (c) and (d) into the reactor, separately;
(4) a method of simultaneously introducing a mixture of the catalyst components (a) and (d) and a mixture of the catalyst components (b) and (c) into the reactor, separately;
(5) a method of simultaneously introducing a mixture of the catalyst components (a) and (b), the catalyst component (c), and the catalyst component (d) into the reactor, separately;
(6) a method of simultaneously introducing a mixture of the catalyst components (c) and (d), the catalyst component (a), and the catalyst component (b) into the reactor, separately;
(7) a method of simultaneously introducing a mixture of the catalyst components (a) and (d), the catalyst component (b), and the catalyst component (c) into the reactor, separately;
(8) a method of simultaneously introducing a mixture of the catalyst components (b) and (c), the catalyst component (a), and the catalyst component (d) into the reactor, separately; and
(9) a method of simultaneously and independently introducing each of the catalyst components (a) to (d) into the reactor, separately.

The aforementioned individual catalyst components (a) to (d) are usually dissolved in the reaction solvent to be used in the low polymerization reaction of ethylene and to be mentioned later and then supplied to the reactor.

[Reaction Solvent]

In the method for producing an α-olefin low polymer of the invention, the low polymerization reaction of the α-olefin is carried out in a reaction solvent.

The reaction solvent is not particularly limited but saturated hydrocarbons are suitably used. Preferably, for example, the solvent is a linear saturated hydrocarbon having 3 to 20 carbon atoms or an alicyclic saturated hydrocarbon having 3 to 20 carbon atoms, such as butane, pentane, 3-methylpentane, n-hexane, n-heptane, 2-methylhexane, octane, cyclohexane, methylcyclohexane, 2,2,4-trimethylpentane, or decalin. In addition, there may be used an aromatic hydrocarbon such as benzene, toluene, xylene, ethylbenzene, mesitylene, or tetralin or an α-olefin low polymer produced by the low polymerization reaction, specifically 1-hexene, decene, or the like obtainable at the trimerization of ethylene. They can be used alone as a single compound or can be also used as a mixed solvent of two or more thereof.

Of these solvents, it is preferred to use a linear saturated hydrocarbon or alicyclic saturated hydrocarbon having 4 to 10 carbon atoms from the viewpoints that formation or precipitation of by-product polymers such as polyethylene can be suppressed and further, a high catalytic activity tends to be obtained. Specifically, n-heptane or cyclohexane is more preferred and most preferred is n-heptane.

The amount of the reaction solvent to be used is not particularly limited but is usually from 0.5 to 5.0 times, preferably from 1.0 to 2.5 times as a weight ratio relative to the supply amount of the raw material α-olefin to be supplied to the reactor.

Here, the supply amount of the raw material α-olefin is equal to the sum of the consumption amount of the raw material α-olefin to be reacted in the reactor and the dissolving amount of the raw material α-olefin to be dissolved in the reaction solvent.

[Conditions for Low Polymerization Reaction]

The reaction temperature of the low polymerization reaction of the α-olefin in the invention is not particularly limited but is usually from 0 to 250° C., preferably from 50 to 200° C., and further preferably from 80 to 170° C.

Moreover, the reaction pressure is not particularly limited but is usually in a range of usually from normal pressure to 25 MPaG, preferably from 0.5 to 15 MPaG, and further preferably from 1 to 10 MPaG.

The residential time in the reactor is not particularly limited but is in a range of usually from 1 minute to 10 hours, preferably from 3 minutes to 3 hours, and further preferably from 5 minutes to 60 minutes.

The reaction type is not particularly limited and may be any of a batch type, a semi-batch type, or a continuous type.

[Production Process of α-Olefin Low Polymer]

The production process of an α-olefin low polymer according to the invention will be described below with reference to FIG. 1 showing one embodiment of the method for producing the α-olefin low polymer of the invention.

In the following description, there may be exemplified a method for producing 1-hexene (a trimer of ethylene) using ethylene as a raw material as the α-olefin. However, the invention is by no means limited to the production of 1-hexene from ethylene.

The apparatus of FIG. 1 mainly comprises a completely mixing and stirring type reactor 10 in which ethylene is subjected to polymerization in the presence of a catalyst, a degassing tank 20 that separates an unreacted ethylene gas from a reaction liquid withdrawn from the reactor 10, an ethylene separation column 30 that distills ethylene in the reaction liquid withdrawn from the degassing tank 20, a high boiling separation column 40 that separates a high-boiling-point substance (hereinafter sometimes referred to as "HB (high boiler)") in the reaction liquid withdrawn from the ethylene separation column 30, and a hexene separation column 50 that conducts distillation of the reaction liquid withdrawn from the column top of the high boiling separation column 40 to distill 1-hexene. Furthermore, a compressor 60 that circulates the unreacted ethylene separated in the degassing tank 20 and a condenser 20A into the reactor 10 via a circulation piping 21 is provided.

In the apparatus of FIG. 1, raw material ethylene is continuously supplied to the reactor 10 from an ethylene supply piping 12a via the compressor 60 and a first supply piping 12. Into the compressor 60, the unreacted ethylene separated in the degassing tank 20 and the condenser 20A is introduced via the circulation piping 21 and also the ethylene separated in the ethylene separation column 30 is introduced via a circulation piping 31. They are circulated into the reactor 10 as raw material ethylene together with the ethylene from the ethylene supply piping 12a. The first supply piping 12 may branch off into a plurality of pipes (e.g., 2 to 8 pipes) before the reactor 10, and then be introduced to the liquid phase part in the reactor (not shown). On the other hand, a reaction solvent to be used in the low polymerization reaction of ethylene is supplied to the reactor 10 from a second supply piping 13. The reaction solvent is one separated and recovered in the hexene separation column 50 at a later stage. Into the second supply piping 13, among the catalyst components, the transition metal atom-containing compound (a) and the nitrogen atom-containing compound (b) are supplied via a catalyst supply piping 13a and the chlorine atom-containing compounds (d) are supplied via a catalyst supply piping 13b, and the catalyst components are introduced into the reactor 10 together with the reaction solvent. A plurality of the catalyst supply pipings 13b may be present (not shown in the figure).

Moreover, the alkylaluminum compound (c) is directly introduced into the reactor 10 from a third supply piping 14. The alkylaluminum compound (c) may be supplied to the reactor 10 after diluted with the reaction solvent of the second supply piping 13 before the catalyst components are supplied from the catalyst supply pipings 13a and 13b (not shown in the figure).

These catalyst components are preferably supplied to the liquid phase part in the reactor 10.

Incidentally, at the time of circulating and supplying the reaction solvent from the hexene separation column 50 to the reactor 10, at least a part of the reaction solvent of the second supply piping 13 before the catalyst components are supplied from the catalyst supply pipings 13a and 13b may be supplied to the vapor phase part of the reactor 10.

As the reactor 10, there may be mentioned a conventionally well-known type one equipped with a stirring machine 10a, a baffle, a jacket, and the like. As the stirring machine 10a, a stirring blade of the type such as paddle, Pfaudler, propeller, turbine, or the like may be used in combination with a baffle such as a planar plate, a cylinder, or a hairpin coil.

Operation conditions of the reactor 10 are the same as the reaction conditions mentioned above.

The trimerization reaction of ethylene is preferably conducted so that a molar ratio ((1-Hexene in reaction liquid)/(Ethylene in reaction liquid)) of 1-hexene to ethylene in the reaction liquid in the reactor 10 becomes from 0.05 to 1.5, and particularly from 0.10 to 1.0. Therefore, it is preferred that in the case of a continuous reaction, catalyst concentration, reaction pressure, and other conditions are controlled so that the molar ratio of 1-hexene to ethylene in the reaction liquid falls within the above range. In the case of a batch reaction, the trimerization reaction of ethylene is preferably stopped at the time when the molar ratio falls within the above range. By conducting the reaction in such a manner, there is a tendency that by-production of components having a boiling point higher than that of 1-hexene is suppressed and thereby selectivity of 1-hexene is further increased.

The reaction product liquid that reaches a predetermined conversion rate in the reactor 10 is continuously withdrawn from the bottom of the reactor 10 via a piping 11 and is supplied to the degassing tank 20. On this occasion, the trimerization reaction of ethylene is terminated by the action of a catalyst deactivator such as 2-ethylhexanol supplied from a deactivator supply piping 11a. The unreacted ethylene degassed in the degassing tank 20 is circulated and supplied to the reactor 10 from an upper part of the degassing tank 20 via a condenser 20A, the circulation piping 21, the compressor 60, and the first supply piping 12. Furthermore, the reaction product liquid from which unreacted ethylene has been degassed is withdrawn from the bottom of the degassing tank 20.

As for operation conditions of the degassing tank 20, usually, the temperature is from 90° C. to 240° C., and preferably from 100° C. to 140° C., and the pressure is from 1 kg/cm$^2$ (normal pressure) to 150 kg/cm$^2$ (0 to 14.6 MPaG), and preferably from normal pressures to 90 kg/cm$^2$ (0 to 8.7 MPaG).

The reaction product liquid withdrawn from the bottom of the degassing tank 20 is supplied to the ethylene separation column 30 by a piping 22. In the ethylene separation column 30, ethylene is distilled and separated from the column top part by distillation, and the ethylene is circulated and supplied to the reactor 10 via the circulation piping 31 and the first supply piping 12. The reaction product liquid from which ethylene has been removed is withdrawn from the column bottom.

As for operation conditions of the ethylene separation column 30, the column top pressure is usually from normal pressures to 30 kg/cm$^2$ (0 to 2.8 MPaG), and preferably from normal pressures to 20 kg/cm$^2$ (0 to 1.9 MPaG) and the reflux ratio (R/D) is usually from 0 to 500, and preferably from 0.1 to 100. The necessary number of theoretical plates is usually from 2 to 20.

The reaction product liquid from which ethylene has been distilled and separated in the ethylene separation column 30 is withdrawn from the column bottom part of the ethylene separation column 30, and is supplied to the high boiling separation column 40 by a piping 32. In the high boiling separation column 40, a high-boiling-point component (HB: high boiler) is withdrawn from the column bottom part via a piping 42 by distillation. Moreover, a distillate in which the high-boiling-point component has been separated is withdrawn from the column top part via a piping 41.

As for operation conditions of the high boiling separation column 40, the column top pressure is usually from 0.1 to 10 kg/cm$^2$ (−0.09 to 0.9 MPaG), and preferably from 0.5 to 5 kg/cm$^2$ (−0.05 to 0.4 MPaG) and the reflux ratio (R/D) is usually from 0 to 100, and preferably from 0.1 to 20. The necessary number of theoretical plates is usually from 3 to 50.

Subsequently, the distillate withdrawn from the column top part of the high boiling separation column 40 is supplied to a hexene separation column 50 by the piping 41. In the hexene separation column 50, 1-hexene is distilled from a piping 51 at the column top part by distillation. Moreover, the reaction solvent, for example, n-heptane is withdrawn from the column bottom part of the hexene separation column 50, and is circulated and supplied as a reaction solvent to the reactor 10 via a solvent circulation piping 52, a pump 13c, and the second supply piping 13.

As for operation conditions of the hexene separation column 50, the column top pressure is usually from 0.1 to 10 kg/cm² (−0.09 to 0.9 MPaG), and preferably from 0.5 to 5 kg/cm² (−0.05 to 0.4 MPaG) and the reflux ratio (R/D) is usually from 0 to 100, and preferably from 0.2 to 20. The necessary number of theoretical plates is usually from 5 to 100.

EXAMPLES

The present invention will be described further specifically based on Examples. Incidentally, the invention is not limited to the following Examples so long as it does not depart from the gist thereof.

In the following Examples, chromium(III)-2-ethylhexanoate used as a transition metal atom-containing compound (a) has one chromium atom in the compound and thus the molar ratios of the first chlorine atom-containing compound (d)-1 and the second chlorine atom-containing compound (d)-2 to the transition metal atom-containing compound (a) become molar ratios of the first chlorine atom-containing compound (d)-1 and the second chlorine atom-containing compound (d)-2 to the transition metal atom in the reaction system as they are.

Example 1

<Preparation of Catalyst Solution>

Into a 500 ml glass-made three-neck flask having a stirring machine, which had been heated and dried at 140° C. for 2 hours or more, 0.37 g (3.9 mmol) of 2,5-dimethylpyrrole and 234 ml of n-heptane were charged under a nitrogen atmosphere, and 8.9 ml (3.9 mmol) of triethylaluminum diluted with n-heptane into 50 g/L was added thereto. Thereafter, the flask was immersed in an oil bath, then the temperature was elevated, and reflux of n-heptane was performed at 98° C. for 3 hours under a nitrogen atmosphere to thereby prepare diethylaluminum (2,5-dimethylpyrrolide) (b) as a nitrogen atom-containing compound. Thereafter, the flask was cooled to 80° C. Subsequently, 6.3 ml (0.65 mmol) of chromium(III)-2-ethylhexanoate (a) diluted with n-heptane into 50 g/L was added. After the addition, the whole was heated and stirred at 80° C. for 30 minutes under a nitrogen atmosphere to prepare a catalyst solution. Thereafter, the catalyst solution was diluted with n-heptane so that the concentration of chromium(III)-2-ethylhexanoate (a) became 0.88 g/L. Incidentally, as n-heptane, one dehydrated with molecular sieves 4 A was used (a dehydrated one was used also as n-heptane to be mentioned later).

<Production of Hexene>

Then, a set of a 500 ml autoclave heated and dried at 140° C. for 2 hours or more was assembled while hot and was subjected to vacuum nitrogen substitution. The following operations were carried out under a nitrogen atmosphere to prevent oxygen and moisture from mixing in. A catalyst feed tube equipped with a pressure-resistant rupture disk was attached to the autoclave. Into the feed tube, 2 ml of the catalyst solution prepared beforehand as above was charged.

Into the body side of the autoclave, n-heptane and respective n-heptane-diluted solutions of triethylaluminum (c), diethylaluminum chloride (d)-1, and 1,1,2,2-tetrachloroethane (d)-2 are charged so as to achieve the molar ratios shown in Table 1. The amount of n-heptane as a reaction solvent became 168 ml in total at the body side (including n-heptane with which each catalyst component was diluted) and further, 5 ml of n-undecane (dehydrated one with molecular sieves 4 A) to be used as an internal standard at compositional analysis by gas chromatography was charged into the body side of the autoclave.

After the autoclave was heated to 140° C., ethylene was introduced from the catalyst feed tube and the low polymerization reaction of ethylene was initiated. During the reaction, the temperature in the autoclave was kept at 140° C. and the total pressure was kept at 7 MPaG.

After 60 minutes, the introduction of ethylene and stirring were stopped and, immediately after the autoclave was promptly cooled, the whole amount of gas was sampled from a vapor phase nozzle. Then, the reaction liquid was sampled and compositional analysis of each sample was performed by gas chromatography. Furthermore, after the reaction liquid was filtrated and dried, the weight of the polymer contained in the reaction liquid was measured.

The catalytic activity was determined by dividing the weight (unit: g) of the reaction product obtained by the reaction for 60 minutes by the amount (unit: g) of the transition metal atom in the transition metal catalyst component (a) used in the reaction.

Table 1 shows the molar ratio of each catalyst component and results.

In the table, the (d) in the "(d)-2/(d)" represents the sum of (d)-1 and (d)-2.

Example 2

All the operations were performed in the same manner as in Example 1 except that the molar ratio of 1,1,2,2-tetrachloroethane (d)-2 to be charged into the body side of the autoclave was changed to 1 mol relative to 1 mol of chromium(III) 2-ethylhexanoate (a). Table 1 shows results.

Example 3

All the operations were performed in the same manner as in Example 1 except that the molar ratio of 1,1,2,2-tetrachloroethane (d)-2 to be charged into the body side of the autoclave was changed to 2 mol relative to 1 mol of chromium(III) 2-ethylhexanoate (a). Table 1 shows results.

Comparative Example 1

All the operations were performed in the same manner as in Example 1 except that 1,1,2,2-tetrachloroethane (d)-2 was not charged into the body side of the autoclave. Table 1 shows results.

The amount of aliphatic hydrocarbon components having 6 carbon atoms (C6, % by weight) in the obtained product and the amount (% by weight) of 1-hexene contained in the above C6 was determined by a gas chromatography.

TABLE 1

| | Catalyst components (molar ratio) | | | | | (d)-2/(d) [mol %] | Catalytic activity [g/g-Cr] | C6 component in product [wt %] | 1-Hexene contained in C6 [wt %] |
|---|---|---|---|---|---|---|---|---|---|
| | (a) | (b) | (c) | (d)-1 | (d)-2 | | | | |
| Example 1 | 1 | 6 | 42 | 12 | 0.5 | 4 | 276000 | 93.2 | 99.0 |
| Example 2 | 1 | 6 | 42 | 12 | 1 | 8 | 314000 | 94.0 | 99.1 |
| Example 3 | 1 | 6 | 42 | 12 | 2 | 14 | 350000 | 94.1 | 99.1 |
| Comparative Example 1 | 1 | 6 | 42 | 12 | 0 | 0 | 207000 | 91.3 | 98.8 |

(a) chromium(III) 2-ethylhexanoate
(b) diethylaluminum (2,5-dimethylpyrrolide)
(c) triethylaluminum
(d)-1 diethylaluminum chloride
(d)-2 1,1,2,2-tetrachloroethane
C6 aliphatic hydrocarbons having 6 carbon atoms

Example 4

All the operations were performed in the same manner as in Example 1 except that 1,1,2,2-tetrachloroethane (d)-2 to be charged into the body side of the autoclave was changed to hexachloroethane (d)-2 and the molar ratio thereof was changed to 1 mol relative to 1 mol of chromium(III) 2-ethylhexanoate (a). Table 2 shows results.

Example 5

All the operations were performed in the same manner as in Example 4 except that the molar ratio of hexachloroethane (d)-2 to be charged into the body side of the autoclave was changed to 2 mol relative to 1 mol of chromium(III) 2-ethylhexanoate (a). Table 2 shows results.

Incidentally, the results of Comparative Example 1 are also described in Table 2.

TABLE 2

| | Catalyst components (molar ratio) | | | | | (d)-2/(d) [mol %] | Catalytic activity [g/g-Cr] | C6 component in product [wt %] | 1-Hexene contained in C6 [wt %] |
|---|---|---|---|---|---|---|---|---|---|
| | (a) | (b) | (c) | (d)-1 | (d)-2 | | | | |
| Example 4 | 1 | 6 | 42 | 12 | 1 | 8 | 257000 | 93.3 | 99.0 |
| Example 5 | 1 | 6 | 42 | 12 | 2 | 14 | 260000 | 94.0 | 99.2 |
| Comparative Example 1 | 1 | 6 | 42 | 12 | 0 | 0 | 207000 | 91.3 | 98.8 |

(a) chromium(III) 2-ethylhexanoate
(b) diethylaluminum (2,5-dimethylpyrrolide)
(c) triethylaluminum
(d)-1 diethylaluminum chloride
(d)-2 hexachloroethane
C6 aliphatic hydrocarbons having 6 carbon atoms

Example 6

All the operations were performed in the same manner as in Example 1 except that the molar ratio of triethylaluminum (c) to be charged into the body side of the autoclave was changed to 54 mol relative to 1 mol of chromium(III) 2-ethylhexanoate (a), diethylaluminum chloride was changed to hexachloroethane (d)-1, and the molar ratio thereof was changed to 6 mol relative to 1 mol of chromium (III) 2-ethylhexanoate (a). Table 3 shows results.

Example 7

All the operations were performed in the same manner as in Example 6 except that the molar ratio of 1,1,2,2-tetrachloroethane (d)-2 to be charged into the body side of the autoclave was changed to 1 mol relative to 1 mol of chromium(III) 2-ethylhexanoate (a). Table 3 shows results.

Example 8

All the operations were performed in the same manner as in Example 6 except that the molar ratio of 1,1,2,2-tetrachloroethane (d)-2 to be charged into the body side of the autoclave was changed to 2 mol relative to 1 mol of chromium(III) 2-ethylhexanoate (a). Table 3 shows results.

Comparative Example 2

All the operations were performed in the same manner as in Example 6 except that 1,1,2,2-tetrachloroethane (d)-2 was not charged into the body side of the autoclave. Table 3 shows results.

<Measurement Method of Chlorine Atom Elimination Rate>

After 15 ml of a solution obtained by diluting hexachloroethane with n-heptane into 0.10 mol/L was added to 60 ml of a solution obtained by diluting triethylaluminum (c) with n-heptane into 0.15 mol/L, the whole was stirred at 80° C. for 2 hours, then remaining concentration of hexachloroethane was analyzed by a gas chromatography, and the chlorine atom elimination rate at which the chlorine atom of hexachloroethane was extracted with triethylaluminum (c) was determined from the remaining amount of hexachloroethane and the reaction time.

When 1.14 mmol that was the remaining amount of hexachloroethane was subtracted from 1.5 mmol that was the amount of charged hexachloroethane, the amount of hexachloroethane from which the chlorine atom was extracted was found to be 0.36 mmol. By dividing the value by 2 hours that was the reaction time, the chlorine atom elimination rate of hexachloroethane was found to be 0.18 mmol/h.

Similarly, as a result of determination of the chlorine atom elimination rate of 1,1,2,2-tetrachloroethane, the rate was found to be 0 mmol/h (Reference: in the same operations, when the temperature was changed from 80° C. to 140° C., the chlorine atom elimination rate of 1,1,2,2-tetrachloroethane was increased to 0.6 mmol/h).

Therefore, (d)-1 is hexachloroethane and (d)-2 is 1,1,2,2-tetrachloroethane.

the body side of the autoclave. Operations other than the above were performed in the same manner as in Example 1. Table 4 shows results.

Comparative Example 3

All the operations were performed in the same manner as in Example 9 except that an n-heptane-diluted solution (3.66 g/L) of 1,1,2,2-tetrachloroethane (d)-2 was not charged into the catalyst feed tube equipped with a pressure-resistant rupture disk of the autoclave and the amount of n-heptane as a reaction solvent to be charged was changed to 168.05 ml in total at the body side of the autoclave. Table 4 shows results.

TABLE 3

| | Catalyst components (molar ratio) | | | | | (d)-2/(d) | Catalytic activity | C6 component in product | 1-Hexene contained in C6 |
|---|---|---|---|---|---|---|---|---|---|
| | (a) | (b) | (c) | (d)-1 | (d)-2 | [mol %] | [g/g-Cr] | [wt %] | [wt %] |
| Example 6 | 1 | 6 | 54 | 6 | 0.5 | 8 | 302000 | 93.8 | 99.0 |
| Example 7 | 1 | 6 | 54 | 6 | 1 | 14 | 362000 | 94.1 | 99.1 |
| Example 8 | 1 | 6 | 54 | 6 | 2 | 25 | 366000 | 94.6 | 99.2 |
| Comparative Example 2 | 1 | 6 | 54 | 6 | 0 | 0 | 270000 | 93.1 | 98.9 |

(a) chromium(III) 2-ethylhexanoate
(b) diethylaluminum (2,5-dimethylpyrrolide)
(c) triethylaluminum
(d)-1 hexachloroethane
(d)-2 1,1,2,2-tetrachloroethane
C6 aliphatic hydrocarbons having 6 carbon atoms Example 9

In Example 1, <Preparation of Catalyst Solution> was not carried out and 0.95 ml of an n-heptane-diluted solution (1.84 g/L, 0.199 g/L as chromium atom) of chromium(III) 2-ethylhexanoate (a), 1.0 ml of an n-heptane-diluted solution (5.16 g/L) of hexachloroethane (d)-1, and 0.5 ml of an n-heptane-diluted solution (3.66 g/L) of 1,1,2,2-tetrachloroethane (d)-2 were charged into a catalyst feed tube equipped with a pressure-resistant rupture disk.

Into the body side of the autoclave, n-heptane and respective n-heptane-diluted solutions of 2,5-dimethylpyrrole (b) and triethylaluminum (c) were charged so as to achieve the molar ratios described in Table 4. The amount of n-heptane as a reaction solvent was controlled to 167.55 ml in total at Comparative Example 4

All the operations were performed in the same manner as in Example 9 except that the amount of an n-heptane-diluted solution (3.66 g/L) of 1,1,2,2-tetrachloroethane (d)-2 to be charged into the catalyst feed tube equipped with a pressure-resistant rupture disk of the autoclave was changed to 1.5 ml and the amount of n-heptane as a reaction solvent to be charged was changed to 166.55 ml in total at the body side of the autoclave. Table 4 shows results.

Figure 2:
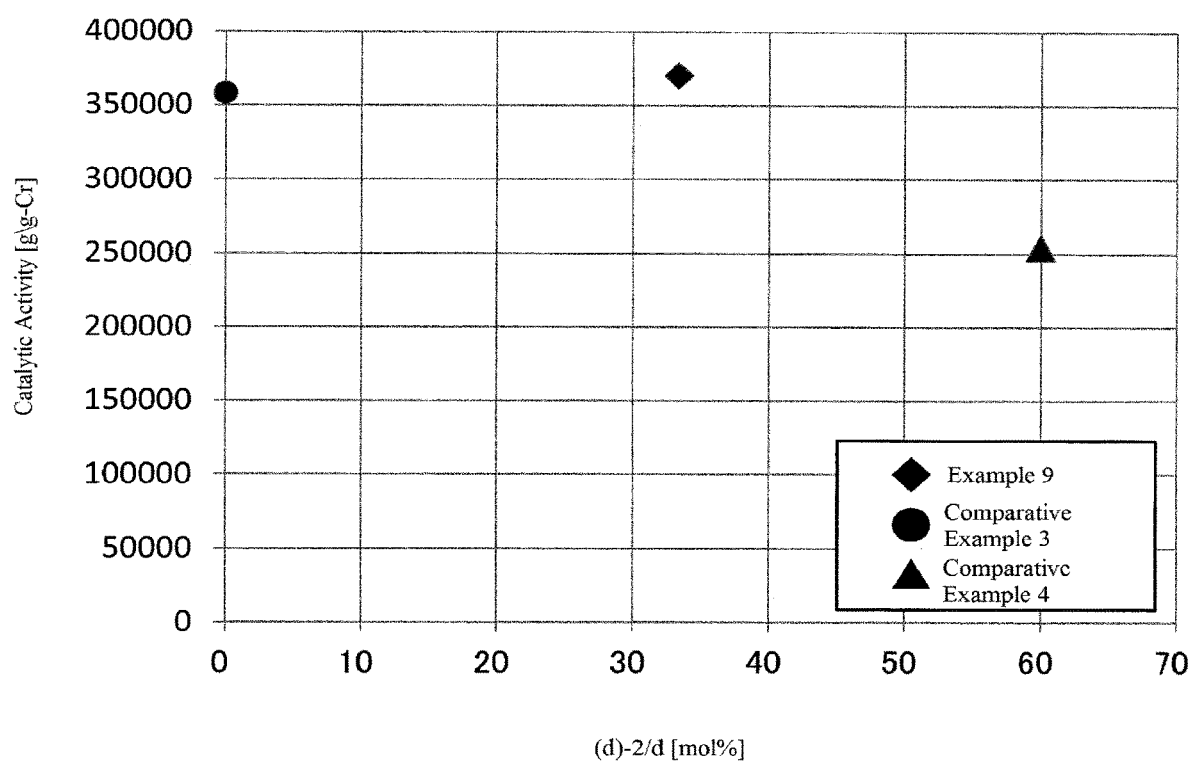
FIG. 2 is a graph showing a relationship between (d)-2/(d) [mol %] and catalytic activity [g/g-Cr] in Example 9 and Comparative Examples 3 and 4.

FIG. 2 shows a relationship between (d)-2/(d) [mol %] and catalytic activity [g/g-Cr] in the above Example 9 and Comparative Examples 3 and 4.

TABLE 4

| | Catalyst components (molar ratio) | | | | | (d)-2/(d) | Catalytic activity | C6 component in product | 1-Hexene contained in C6 |
|---|---|---|---|---|---|---|---|---|---|
| | (a) | (b) | (c) | (d)-1 | (d)-2 | [mol %] | [g/g-Cr] | [wt %] | [wt %] |
| Example 9 | 1 | 6 | 60 | 6 | 3 | 33 | 370000 | 95.2 | 99.3 |
| Comparative Example 3 | 1 | 6 | 60 | 6 | 0 | 0 | 358000 | 93.8 | 99.1 |
| Comparative Example 4 | 1 | 6 | 60 | 6 | 9 | 60 | 254000 | 96.6 | 99.4 |

(a) chromium(III) 2-ethylhexanoate
(b) 2,5-dimethylpyrrole
(c) triethylaluminum
(d)-1 hexachloroethane
(d)-2 1,1,2,2-tetrachloroethane
C6 aliphatic hydrocarbons having 6 carbon atoms

Example 10

In Example 1, <Preparation of Catalyst Solution> was not carried out and 0.95 ml of an n-heptane-diluted solution (1.84 g/L, 0.199 g/L as chromium atom) of chromium(III) 2-ethylhexanoate (a) and 0.1 ml of an n-heptane-diluted solution (3.68 g/L) of 1,1,2,2-tetrachloroethane (d)-2 were charged into a catalyst feed tube equipped with a pressure-resistant rupture disk.

Into the body side of the autoclave, n-heptane and respective n-heptane-diluted solutions of 2,5-dimethylpyrrole (b), triethylaluminum (c), and diethylaluminum chloride (d)-1 were charged so as to achieve the molar ratios described in Table 5. The amount of n-heptane as a reaction solvent was controlled to 168.95 ml in total at the body side of the autoclave. Operations other than the above were performed in the same manner as in Example 1. Table 5 shows results.

Example 11

All the operations were performed in the same manner as in Example 10 except that the amount of an n-heptane-diluted solution (3.68 g/L) of 1,1,2,2-tetrachloroethane (d)-2 to be charged into the catalyst feed tube equipped with a pressure-resistant rupture disk of the autoclave was changed to 1.0 ml and the amount of n-heptane as a reaction solvent to be charged was changed to 168.05 ml in total at the body side of the autoclave. Table 5 shows results.

Example 12

All the operations were performed in the same manner as in Example 10 except that the amount of an n-heptane-diluted solution (3.68 g/L) of 1,1,2,2-tetrachloroethane (d)-2 to be charged into the catalyst feed tube equipped with a pressure-resistant rupture disk of the autoclave was changed to 1.6 ml and the amount of n-heptane as a reaction solvent to be charged was changed to 167.45 ml in total at the body side of the autoclave. Table 5 shows results.

Comparative Example 5

All the operations were performed in the same manner as in Example 10 except that an n-heptane-diluted solution (3.68 g/L) of 1,1,2,2-tetrachloroethane (d)-2 was not charged into the catalyst feed tube equipped with a pressure-resistant rupture disk of the autoclave and the amount of n-heptane as a reaction solvent to be charged was changed from 168.95 ml in total to 169.05 ml in total at the body side of the autoclave. Table 5 shows results.

Comparative Example 6

All the operations were performed in the same manner as in Example 10 except that the amount of an n-heptane-diluted solution (3.68 g/L) of 1,1,2,2-tetrachloroethane (d)-2 to be charged into the catalyst feed tube equipped with a pressure-resistant rupture disk of the autoclave was changed to 2.5 ml and the amount of n-heptane as a reaction solvent to be charged was changed to 166.55 ml in total at the body side of the autoclave. Table 5 shows results.

Figure 3:
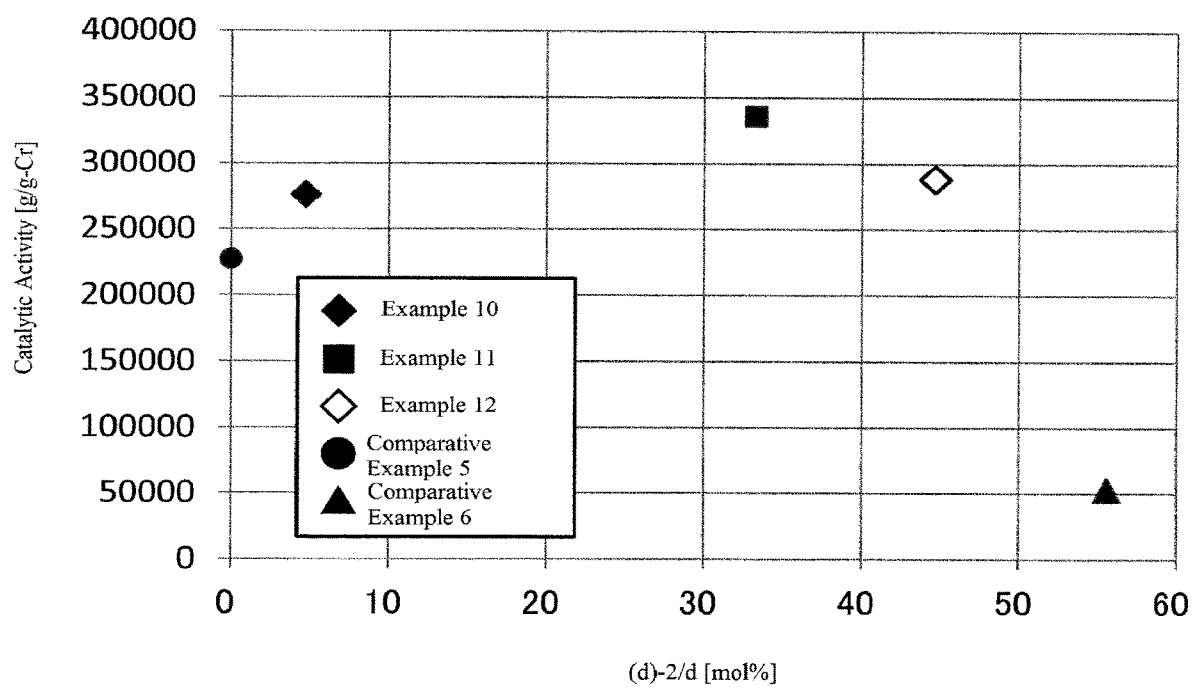
FIG. 3 is a graph showing a relationship between (d)-2/(d) [mol %] and catalytic activity [g/g-Cr] in Examples 10 to 12 and Comparative Examples 5 and 6.

FIG. 3 shows a relationship between (d)-2/(d) [mol %] and catalytic activity [g/g-Cr] in the above Examples 10 to 12 and Comparative Examples 5 and 6.

TABLE 5

| | Catalyst components (molar ratio) | | | | | (d)-2/(d) [mol %] | Catalytic activity [g/g-Cr] | C6 component in product [wt %] | 1-Hexene contained in C6 [wt %] |
|---|---|---|---|---|---|---|---|---|---|
| | (a) | (b) | (c) | (d)-1 | (d)-2 | | | | |
| Example 10 | 1 | 6 | 48 | 12 | 0.6 | 5 | 276000 | 93.3 | 98.9 |
| Example 11 | 1 | 6 | 48 | 12 | 6 | 33 | 336000 | 95.5 | 99.3 |
| Example 12 | 1 | 6 | 48 | 12 | 9.7 | 45 | 288000 | 96.1 | 99.4 |
| Comparative Example 5 | 1 | 6 | 48 | 12 | 0 | 0 | 227000 | 92.6 | 98.8 |
| Comparative Example 6 | 1 | 6 | 48 | 12 | 15 | 56 | 53000 | 98.6 | 99.6 |

(a) chromium(III) 2-ethylhexanoate
(b) 2,5-dimethylpyrrole
(c) triethylaluminum
(d)-1 diethylaluminum chloride
(d)-2 1,1,2,2-tetrachloroethane
C6 aliphatic hydrocarbons having 6 carbon atoms From the above results, it is understood that catalytic activity can be increased and the yield and selectivity of the α-olefin low polymer can be enhanced by using the first chlorine atom-containing compound (d)-1 and the second chlorine atom-containing compound (d)-2 in predetermined ratios as chlorine atom-containing compounds (d).

While the invention has been described in detail and with reference to specific embodiments thereof, it will be apparent to one skilled in the art that various changes and modifications can be made therein without departing from the spirit and scope thereof.

The present application is based on Japanese Patent Application No. 2015-066777 filed on Mar. 27, 2015, and the contents are incorporated herein by reference.

EXPLANATION OF REFERENCE SIGNS

10 . . . Reactor
10a . . . Stirring machine
20 . . . Degassing tank
30 . . . Ethylene separation column
40 . . . High boiling separation column
50 . . . Hexene separation column
60 . . . Compressor

The invention claimed is:
1. A method for producing an α-olefin oligomer, the method comprising:

oligomerizing an α-olefin in the presence of i) a catalyst comprising a transition metal-containing compound (a), a nitrogen-containing compound (b), an alkylaluminum compound (c) and chlorine-containing compounds (d), and ii) a reaction solvent to produce the α-olefin oligomer, wherein:

the chlorine-containing compounds (d) comprise at least one first chlorine-containing compound (d)-1 selected from the group consisting of diethylaluminum chloride and hexachloroethane, and a second chlorine-containing compound (d)-2 which is 1,1,2,2-tetrachloroethane;

the chlorine containing compounds (d) is supplied at an amount, relative to the transition metal-containing compound (a), in the range of 2 molar equivalents to 50 molar equivalents in the oligomerizing;

the ratio of the second chlorine containing compound (d)-2 to the total amount of the chlorine-containing compounds (d) is 1 mol % or more and 49 mol % or less;

the second chlorine-containing compound (d)-2 has the lowest chlorine atom elimination rate among the chlorine-containing compounds (d); and the chlorine atom elimination rate is determined by reacting the chlorine-containing compounds (d)-1 and (d)-2 with the alkylaluminum compound (c) under stirring at 80° C. for a reaction period of 2 hours and dividing the difference between the remaining amount of (d)-1 and (d)-2 and the initial amount of (d)-1 and (d)-2, respectively.

2. The method according to claim 1, wherein the alkylaluminum compound (c) is triethylaluminum.

3. The method according to claim 1, wherein the transition metal in the transition metal containing compound (a) comprises chromium and the nitrogen containing compound (b) comprises a pyrrole compound.

4. The method according to claim 1, wherein the α-olefin is ethylene and the α-olefin oligomer is 1-hexene.

5. The method according to claim 1, wherein the ratio of the second chlorine containing compound (d)-2 to the total amount of the chlorine containing compounds (d) is 4 mol % or more and 40 mol % or less.

6. The method according to claim 1, wherein the catalytic activity of the oligomerizing is higher than a reference oligomerizing which is identical to the oligomerizing except that the second chlorine containing compound (d)-2 is not used, provided that the catalytic activity is determined by dividing a weight (unit: g) of the α-olefin oligomer produced by the oligomerizing for 60 minutes by the amount (unit: g) of the transition metal in the transition metal-containing component (a).

* * * * *

UNITED STATES PATENT AND TRADEMARK OFFICE
CERTIFICATE OF CORRECTION

Page 1 of 1

PATENT NO. : 10,689,310 B2
APPLICATION NO. : 15/715505
DATED : June 23, 2020
INVENTOR(S) : Hiroki Emoto It is certified that error appears in the above-identified patent and that said Letters Patent is hereby corrected as shown below:

On the Title Page

Item (30), the Foreign Application Priority Data information is incorrect. Item (30) should read:
--(30) Foreign Application Priority Data
Mar. 27, 2015 (JP)………………. 2015-066777--

Signed and Sealed this
Twenty-eighth Day of July, 2020

Andrei Iancu
*Director of the United States Patent and Trademark Office*